United States Patent [19]

Yarger et al.

[11] Patent Number: 5,068,120
[45] Date of Patent: Nov. 26, 1991

[54] AMINE ESTER DERIVATIVES AS LOW CALORIE FAT MIMETICS

[75] Inventors: Ronald G. Yarger, Covent Station; Lawrence P. Klemann, Somerville; John W. Finley, Whippany, all of N.J.

[73] Assignee: Nabisco Brands, Inc., Parsippany, N.J.

[21] Appl. No.: 561,099

[22] Filed: Aug. 1, 1990

[51] Int. Cl.$^5$ .............................................. A23D 9/00
[52] U.S. Cl. .................................. 426/611; 260/404; 260/404.5; 426/603; 426/612
[58] Field of Search ............... 426/601, 603, 606, 611, 426/612, 531; 260/404.5, 404

[56] References Cited

U.S. PATENT DOCUMENTS

| | | | |
|---|---|---|---|
| 519,980 | 5/1894 | Winter | |
| 2,962,419 | 11/1960 | Minich | 167/81 |
| 3,495,010 | 2/1970 | Fossel | 424/312 |
| 3,579,548 | 5/1971 | Whyte | 260/410.7 |
| 3,600,186 | 8/1971 | Mattson et al. | 99/1 |
| 3,637,774 | 1/1972 | Babyan et al. | 260/410.6 |
| 3,876,794 | 4/1975 | Rennhard | 426/152 |
| 4,005,195 | 1/1977 | Jandacek | 424/180 |
| 4,304,768 | 2/1981 | Staub | 424/180 |
| 4,508,746 | 4/1985 | Hamm | 426/601 |
| 4,582,927 | 4/1986 | Fulcher | 560/201 |
| 4,797,300 | 1/1989 | Jandacek et al. | 426/549 |
| 4,830,787 | 5/1989 | Klemann | 260/410 |
| 4,840,815 | 6/1989 | Meyer et al. | 426/611 |
| 4,849,242 | 7/1989 | Kershner | 426/601 |
| 4,861,613 | 8/1989 | White et al. | 426/611 |
| 4,915,974 | 4/1990 | D'Amelia et al. | 426/611 |
| 4,927,659 | 5/1990 | Klemann et al. | 426/611 |

FOREIGN PATENT DOCUMENTS

| | | |
|---|---|---|
| 1106681 | 8/1981 | Canada . |
| 0205273 | 5/1986 | European Pat. Off. . |
| 0233856 | 2/1987 | European Pat. Off. . |
| 3529564 | 4/1979 | Fed. Rep. of Germany . |
| 2021579 | 3/1987 | United Kingdom . |

OTHER PUBLICATIONS

Streitwieser, A. and Heathcock, C. H., Introduction to Organic Chemistry, 1981, p. 567, Macmillan Publishing Co., Inc. New York.
Oette, K., and Tschung, T. S., Hoppe-Seyler's Z. Physiol. Chem. 361: 1179-1191 (1980). Translation only.
Booth, A. N., and Gros, A. T., J. Amer. Oil Chem. Soc. 40: 551-553 (1963).
Garner, C. W., and Smith, L. C., Biochem Biophys. Res. Commun. 39: 672-682 (1970).
Goodman and Gilman's Pharmacological Basis of Therapeutics 7th ed., Macmillan Pub., Co., N. Y. 1002-1003 (1985).
Gottenbos, J. J., Chapter 8 in Beare-Rogers, J., ed., "Dietary Fat Requirements in Health and Developement" A. O. C. S. 107-112 (1988).
Hamm, D. J., Food Sci. 49: 419-428 (1984).
Haumann, B. J., J. Amer. Oil Chem. Soc. 63: 278-288 (1986).
Hess, K., and Messmer, E., Ber. 54B: 499-523 (1921). (full German text and English translation).
LaBarge, R. G. Food Tech., 42: 84-90 (1988).
Mead, J., et al., Lipids, Plenum, New York, pp. 459-470 (1986).
Oette, K., and Tschung, T. S., Hoppe-Seyler's Z. Physiol. Chem. 361: 1179-1191 (1980).
Stryker, W. A., Arch. Path. 31: 670-692 (1941).

Primary Examiner—Donald E. Czaja
Assistant Examiner—Leslie Wood

[57] ABSTRACT

Amine ester derivatives of the general formula:

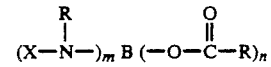

where
B is an organic radical having from 2 to 12 carbons,
each R is, independently, an aliphatic group having 1 to 30 carbons,
X=H or R, independently,
m=1 to 2, and
n=1 to 7 comprise a new class of low calorie fat mimetics. Methods of using and edible compositions incorporating the new fat mimetics are disclosed.

23 Claims, No Drawings

AMINE ESTER DERIVATIVES AS LOW CALORIE FAT MIMETICS

BACKGROUND OF THE INVENTION

This invention relates to the use of amine ester derivatives as low calorie fat mimetics. These compounds have a ($C_2$ to $C_{12}$) backbone to which are attached one or two amine groups and one to seven aliphatic groups in ester linkage.

Dietary fat is the most concentrated source of energy of all the nutrients, supplying 9 kcal/gram, about double that contributed by either carbohydrate or protein. The amount of fat in the American diet has increased in the last 60 years by about 25% (Mead, J., et al. Lipids, Plenum, New York, 1986, page 459), so that fats now provide approximately 40% of the daily caloric intake. Moreover, technological advances in the food industry, including efficient and safe hydrogenation procedures, have changed the kind of fat in foods.

Because fats are high in calories and because certain fats appear to pose a health risk when consumed in large quantities over time, a number of national advisory committees on nutrition have made recommendations differing in detail, but the common theme is a reduction in the total amount of fat in the diet (Gottenbos, J. J., chapter 8 in Beare-Rogers, J., ed., *Dietary Fat Requirements in Health and Development*, A.O.C.S. 1988, page 109). Yet fat contributes to the palatability and flavor of food, since most food flavors are fat-soluble, and to the satiety value, since fatty foods remain in the stomach for longer periods of time than do foods containing protein and carbohydrate. Furthermore, fat is a carrier of the fat-soluble vitamins, A, D, E, and K, and the essential fatty acids, which have been shown to be important in growth and in the maintenance of many body functions. Hence, major research efforts have focused on ways to produce food substances that provide the same functional and organoleptic properties as fats, but not the calories.

A number of fat replacements have heretofore been suggested (recently reviewed by Hamm, D. J., *J. Food Sci.* 49: 419–428 (1984), Haumann, B. J., *J. Amer. Oil Chem. Soc.* 63: 278–288 (1986) and LaBarge, R. G., *Food Tech.* 42: 84–90 (1988)). Hamm divides replacement fats into two broad categories: structurally re-engineered triglycerides modified to retain their conventional functional properties in foods, while removing their susceptibility toward hydrolysis or subsequent absorption during digestion, and materials developed from chemistry unrelated to triglycerides.

Examples of the former class of triglyceride analogues include compounds having the glycerol moiety replaced with alternate polyols (e.g., pentaerythritol in U.S. Pat. No. 2,962,419 to Minich, or sugars, suggested by Hess, K., and Messmer, E., Ber. 54B: 499–523 (1921), and patented years later by Mattson and Volpenhein, U.S. Pat. No. 3,600,186, and Meyer, et al., U.S. Pat. No. 4,840,815); compounds having the fatty acids replaced with alternate acids (e.g., branched esters as described in U.S. Pat. No. 3,579,548 to Whyte); compounds having insertions between the glycerol and the fatty acid e.g., ethoxy or propoxy groups in U.S. Pat. No. 4,861,613 to White and Pollard); compounds having reversed esters (e.g., malonates in U.S. Pat. No. 4,582,927 to Fulcher and trialkoxytricarballylates in U.S. Pat. No. 4,508,746 to Hamm); and compounds having the ester bonds replaced by ether bonds (Can. Pat. No. 1,106,681 to Trost).

Examples of Hamm's second category of fat replacements chemically unrelated to triglycerides are mineral oil (suggested as early as 1894 in U.S. Pat. No. 519,980 to Winter); polyglucose and polymaltose (U.S. Pat. No. 3,876,794 to Rennhard); jojoba wax (W. Ger. Pat. No. 3,529,564 to Anika); polyoxyalkylene esters (U.S. Pat. No. 4,849,242 to Kershner); polyvinyl alcohol esters (U.S. Pat. No. 4,915,974 to D'Amelia and Jacklin); and polysiloxane (Eur. Pat. Ap. No. 205,273 to Frye).

Nondigestible or nonabsorbable edible fat replacements have proved disappointing when tested in feeding trials, where gastrointestinal side effects occurred, in some cases so extreme that frank anal leakage was observed. Nondigestible fats appear to act as a laxative and are expelled from the body, eliciting foreign body reactions like those early documented for mineral oil (Stryker, W. A., Arch. Path. 31: 670–692 (1941), more recently summarized in Goodman and Gilman's Pharmacological Basis of Therapeutics, 7th ed., Macmillan Pub. Co., N.Y. 1985, pp. 1002–1003). Similarly, a series of experimental fats, e.g., glyceride esters of dibasic acids, synthesized by U.S.D.A. in the 1960's exhibited undesirable gastrointestinal side effects when the compounds were fed to rats (Booth, A. N., and Gros, A. T., *J. Amer. Oil Chem. Soc.* 40: 551–553 (1963)); in several of the balance studies, the diarrhea was so extreme that digestibility coefficients could not be calculated (ibid., Table I, p. 552).

Polyglycerol and polyglycerol esters, suggested as fat replacements by Babayan and Lehman (U.S. Pat. No. 3,637,774), have been suggested for use as fecal softening agents as well (U.S. Pat. No. 3,495,010 to Fossel). A number of remedies have been recommended to combat the anal leakage observed when sucrose polyesters are ingested (e.g., employing cocoa butters, U.S. Pat. No. 4,005,195 to Jandacek, incorporating saturated fatty groups, Eur. Pat. Ap. No. 233,856 to Bernhardt, or mixing residues, U.S. Pat. No. 4,797,300 to Jandacek, et al.), and dietary fiber preparations have been incorporated into polysaccharide and/or polyol-containing foodstuffs to help inhibit the diarrheal effect (U.S. Pat. No. 4,304,768 to Staub et al.). Partially digestible fat replacements have also been suggested (U.S. Pat. No. 4,830,787 to Klemann and Finley; U.S. Pat. No. 4,849,242, cited above; and U.S. Pat. No. 4,927,659 to Klemann, et al.).

SUMMARY OF THE INVENTION

An object of the present invention is to provide a new group of edible fat replacement compounds having an array of functional groups that can be selected to tailor the properties of the compounds and modulate caloric availability while minimizing laxative side effects.

These and other objects are accomplished by the present invention, which describes the use of amine ester compounds comprising a new class of edible synthetic fat mimetics, methods of using them, and food compositions incorporating them. These compounds have an organic backbone to which is attached at least one aliphatic group in ester linkage and at least one amine group.

The new fat mimetics may be described by the general formula:

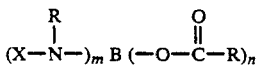

where
B is an organic radical having from 2 to 12 carbons,
each R is, independently, an aliphatic group having 1 to 30 carbons,
X=H or R, independently,
m=1 to 2, and
n=1 to 7.

DETAILED DESCRIPTION OF THE INVENTION

Garne and Smith synthesized dioctanoyl 2-amino-1-propanol to use as a substrate for lipase (in a study conducted in monomolecular films, Garner, C. W., and Smith, L. C., *Biochem. Biophys. Res. Commun.* 39: 672-682 (1970)). Oette and Tschung subsequently suggested aminoglyceride derivatives as phospholipid analogues of possible pharmacological utility in promoting the in vivo formation of natural phospholipids (Gt. Brit. Pat. No. 2,021,579, page 5, line 23). When fed to rats, aminomonoglyceride derivatives were found to be metabolized and accumulated in organ lipids, mostly in the liver, but also in adipose tissue (Oette, K., and Tschung, T. S., *Hoppe-Seyler's Z. Physiol. Chem.* 361: 1179-1191 (1980)). The authors concluded that these monoglyceride analogues were metabolized to lecithin and cephalin analogues (GB 2,021,579, page 5, line 6).

The present invention is based on the finding that amine ester derivatives, compounds having an organic radical backbone comprising 2 to 12 carbons to which are attached at least one and up to seven aliphatic groups in ester linkage, and one to two amine groups are useful as edible fat mimetics.

The amine ester derivatives of this invention comprise compounds having the following general formula:

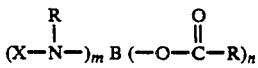

where
B is an organic radical having from 2 to 12 carbons,
each R is, independently, an aliphatic group having 1 to 30 carbons,
X =H or R, independently,
m=1 to 2, and
n =1 to 7.

The compounds of this invention have a backbone B to which are attached at least one aliphatic group (R) in ester linkage (—O (CO)—R); the compounds may additionally have up to seven such groups so attached. The compounds further have at least one and as many as two amine groups (—NRX). Since each nitrogen has one R and one X, and X may be either hydrogen or an aliphatic R group, the amine may be secondary or tertiary.

Backbone B, generally derived from an alkanolamine, may be linear, branched, carbocylic or heterocyclic. Examples of alkanolamines forming the compound backbones are aminoethanol, aminopropanol, aminopropanediol, diaminopropanol, aminobutanol, diaminobutanol, aminobutanediol, diaminobutanediol, aminopentanol, diaminopentanol, aminopentanediol, diaminopentanediol, aminohexanol, diaminohexanol, aminohexanediol, and diaminohexanediol. Chemical descriptions and formulae used here include isomeric variations.

As mentioned above, backbone B may also be carbocyclic or heterocyclic rather than acyclic. This invention encompasses cyclohexyl derivatives having a six-membered carbon ring (which may be saturated or unsaturated) to which is attached at least one aliphatic group in ester linkage and at least one aliphatic group in amine linkage as described in the general formula above. Thus, aminocyclohexanols, diaminocyclohexanols, aminocyclohexanediols, diaminocyclohexanediols, their cyclohexene counterparts, and the like may form the compound backbones.

This invention further encompasses amine ester sugar derivatives such as those derived from ribose, mannose, glucose, lactose, sucrose, fructose, galactose, and the like, wherein R is a heterocyclic to which is attached at least one aliphatic group in ester linkage and at least one amine linkage, such as, for example, glucosamine, galactosamine or amino-deoxyribose amine esters, and the like.

The aliphatic groups (R) may be linear or branched, saturated or unsaturated. R groups are generally derived from natural or synthetic fatty acids of the formula RCOOH, where R is an aliphatic group having 1 to 30 carbons. Examples of fatty acids are acetic, propionic, butyric, caproic, caprylic, pelargonic, capric, undecanoic, lauric, myristic, palmitic, stearic, arachidic, behenic, erucic, brassidic, lignoceric, cerotic, montanic, melissic, palmitoleic, oleic, vaccenic, linoleic, linolenic, eleostearic, arachidonic, nervonic, eicosapentaenoic, docosatetraenoic, docosapentaenoic, docosahexaenoic, and the like acids.

Mixtures of fatty acids may also be used, such as those obtained from the hydrolysis of non-hydrogenated, partially hydrogenated or fully hydrogenated soybean, safflower, sunflower, high oleic sunflower, sesame, peanut, corn, olive, rice bran, canola, babassu nut, coconut, palm, palm kernel, lupin, nasturtium seed, mustard seed, cottonseed, low erucic rapeseed or marine oils. Fatty acids derived from other fats, such as dairy butterfat, tallow or lard, or plant waxes such as jojoba may be employed. Specific fractions of natural or processed oils, fats or waxes may also be used.

The compounds of this invention may be synthesized beginning with a polyfunctional structure containing amine and hydroxyl residues. Addition of an alkyl halide (preferably a bromide or iodide) in a solvent that promotes nucleophilic displacement reactions and application of heat produces an alkyl amine functionality. Addition of a fatty acid chloride in the presence of a solvent such as pyridine affords a fat-like substance containing alkyl amine and carboxylic ester moieties.

Alternatively, the synthesis may begin with an alkylaminoalcohol. Addition of an appropriate amount of fatty acid chloride to the alkylaminoalcohol in the presence of a solvent such as pyridine affords a fat-like substance containing carboxylic ester and alkylamine moieties. Example syntheses are set forth in the next section.

As is apparent from the general formula and the syntheses, this invention includes compounds with one or more nitrogen atoms partially or fully substituted with aliphatic groups, or mixtures of these.

The R groups are selected to provide a discernible fatty character in the compounds. Thus, most of the R groups have 2 to 5 or more carbon atoms, with a majority containing 3 to 23, more narrowly 9 to 19, and even more narrowly, 15 to 17 carbon atoms. Preferred ester amine compounds can have an array of R groups selected to include 95% derived from acids having 14 to 18 carbon atoms. In one embodiment, the R should be predominantly saturated and derived from $C_{14}$ to $C_{18}$ acids. In another embodiment, the R should be predominantly derived from unsaturated $C_{16}$ to $C_{18}$ acids (with a preponderance of monounsaturated groups).

The choice, number and arrangement of R groups on the amine ester derivatives will affect the biological as well as physical properties of the compounds. Some compounds of this invention are noncaloric. Where any of the groups are hydrolyzed, the caloric value of the compound may increase. Where a group is metabolized, it may be a highly desirable or essential fatty acid residue such as linoleic acid.

Some compounds are partially digestible. By this is meant that the compounds deliver less than 9 kcal/gram, preferably less than 5, and, in some embodiments, less than 3 kcal/gram, upon being metabolized.

The amine ester compounds of this invention may be incorporated either alone, or in combination with another fat and/or fat mimetic, into any food composition or used in conjunction with any edible material. Other fats include natural triglycerides rich in highly desirable or essential fatty acids, such as oleic, linoleic, linolenic, or eicosapentaenoic acid, triglycerides bearing fatty acids having beneficial attributes such as those associated with conjugated linoleic acid isomers, medium chain triglycerides and the like. Other fat mimetics include any heretofore suggested as edible fat replacements, including, but not limited to, sugar esters, neoalkyl esters, polyglycerol esters, malonate esters, propoxylated glycerols, retrofats, carboxy/carboxylates, polyvinyl alcohol esters, and the like.

The term "edible material" is broad and includes anything edible, whether or not intended for nutrition, e.g., it can be an additive such as an antioxidant for fats or oils, an antispatter agent, an emulsifier, a texture modifier such as a plasticizer for chewing gum, a component for cosmetics, or other minor functional ingredient such as a carrier or diluent for use in flavorings, pharmaceuticals, and the like.

Representative of fat-containing food products which can contain, in addition to other edible ingredients, the amine ether compounds of this invention in full or partial replacement of natural or synthetic fat are: frozen desserts, e.g., frozen novelties, ice cream, ices, sherbet, or milk shakes; puddings and pie fillings; margarine substitutes or blends; flavored bread or biscuit spreads; mayonnaises and mustards; salad dressings; filled dairy products such as filled cream or filled milk; dairy or non-dairy cheese spreads; coffee lighteners, liquid and dried; flavored dips; frying fats and oils; reformed and comminuted meats; meat substitutes or extenders; pet foods; egg products and substitutes; whipped toppings; compound coatings; frostings and fillings; nut products such as peanut butter; cocoa butter replacements or blends; candy, especially fatty candies such as those containing peanut butter or chocolate; chewing gum; breakfast cereals; bakery products, e.g., cakes, breads, rolls, pastries, cookies, biscuits, and crackers; mixes or ingredient premixes for any of these; as well as flavor, nutrient, drug or functional additive delivery systems.

The following is a list of representative, but not limiting, examples of amine esters of this invention:

(A) Amine esters comprising compounds having an aliphatic backbone of 2 to 6 carbons to which are attached one to three aliphatic groups in ester linkage, and one or two amine groups. Examples of this class include

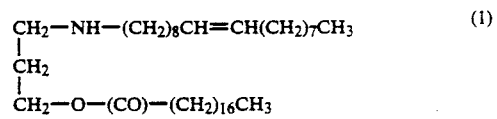

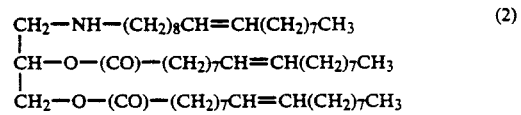

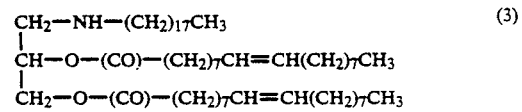

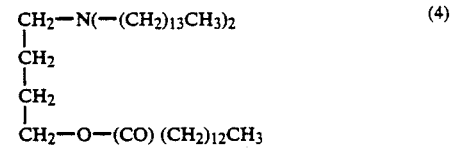

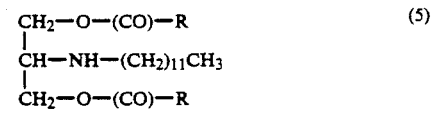

where the R groups are derived from hydrogenated corn oil fatty acids

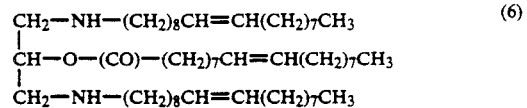

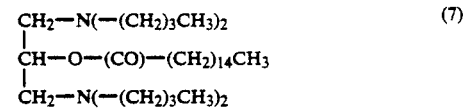

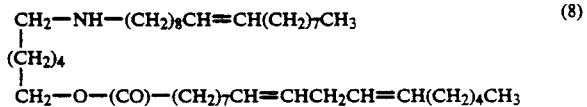

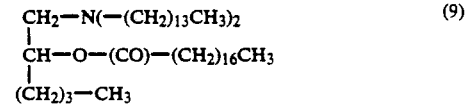

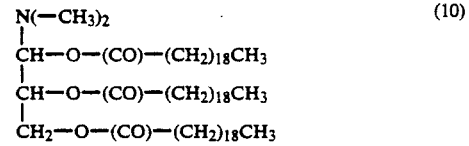

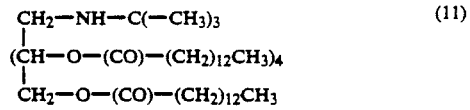

-continued

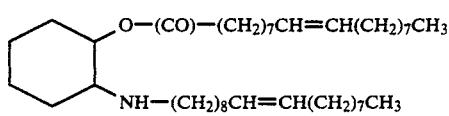 (12)

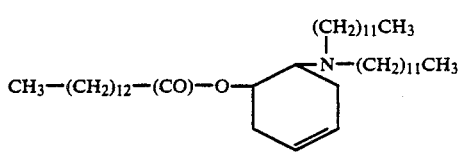 (13)

(B) Amine esters comprising compounds having a backbone of 5 to 12 carbons to which are attached one or two amine, and one to seven aliphatic groups in ester linkage. Examples of this class include

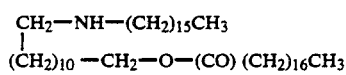 (14)

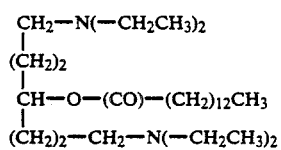 (15)

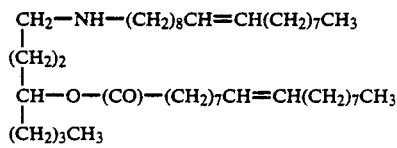 (16)

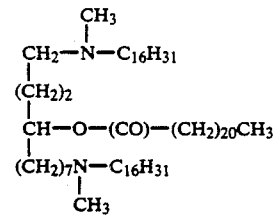 (17)

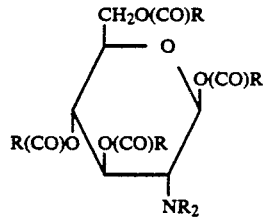 (18)

where R is derived from safflower oil

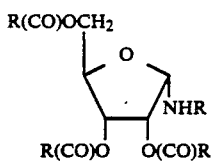 (19)

where R is derived from soybean oil

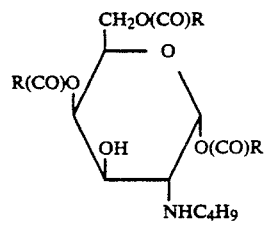 (20)

where R = —$(CH_2)_{14}CH_3$ (21)

where R is derived from sunflower oil

EXAMPLES

The following examples are presented to further illustrate and explain the present invention and should not be taken as limiting in any regard. Unless otherwise indicated, all parts and percentages are by weight, and are based on the weight at the particular stage of the processing being described.

EXAMPLE 1

In this example, N-stearyl-2,3-dioleoyloxy-1-aminopropane, an amine ester depicted in structure (3) above, is prepared.

To a rapidly stirred solution of 3.43 g (0.01 mole) of N-stearyl-2,3-dihydroxy-1-aminopropane in 25 mL of dry pyridine at room temperature is added 6.02 g (0.02 mole) of freshly distilled oleoyl chloride. The reaction mixture is heated to 60° C. for one hour, then cooled. It is diluted with 50 mL ethyl acetate, washed with 5% HCl (2×30 mL), water (2×30 mL), dried over magnesium sulfate, and filtered. Evaporation of the solvent affords crude material that is purified by silica gel chromatography (hexane/ethyl acetate; 40/1 v/v)) to yield the title compound.

EXAMPLE 2

This example describes the synthesis of another amine ester of this invention, N-t-butyl-2,3,4,5,6-pentamyristoyloxy- 1-aminohexane (depicted in structure (11) above).

To a magnetically stirred solution of 2.37 g (0.01 mole) of N-t-butyl-2,3,4,5,6-pentahydroxy-1-aminohexane in 50 mL dry pyridine is added 12.24 g (0.05 mole) of myristoyl chloride. The reaction mixture is heated to 60.C for three hours, then cooled. It is diluted with 50 mL ethyl acetate, washed with 5% HCl (3×60 mL), then water (3×60 mL), dried over magnesium sulfate, and filtered. Evaporation of the solvent affords crude material that is chromatographed on silica gel, using hexane/ethyl acetate (40/1; v/v) as eluent. Combination and concentration of appropriate fractions yields the title compound.

EXAMPLE 3

In this example, N-dodecyl-1,3-diacyloxy-2-aminopropane, an amine ester depicted in structure (5) above, is prepared.

An acid chloride mixture, 600 g, that is derived from treating hydrogenated corn oil fatty acids with oxalyl chloride is added, dropwise, to 287 g of N-dodecyl-1,3-dihydroxy-2-aminopropane. The reaction mixture is stirred under vacuum (-30 Torr) for four hours, venting the HCl vapor through a potassium hydroxide trap. The mixture is then passed through a falling film distillation apparatus (using mesitylene as reflux solvent) to remove excess acid chloride, which affords the title compound as a viscous amber oil.

EXAMPLE 4

Filled Cream. To make a "filled cream" composition, homogenize about

| Ingredient | parts |
|---|---|
| Example 1 Amine Ester | 30.0 |
| Skim Milk | 69.9 |
| Polysorbate 80 | 0.1 | in a conventional dairy homogenizer.

EXAMPLE 5

Filled Milk. To prepare a "filled milk" composition, combine about

| Ingredient | parts |
|---|---|
| Example 4 Filled Cream | 100 |
| Skim Milk | 900 | and rehomogenize.

EXAMPLE 6

Low Calorie Milk. A low calorie "whole milk" may be prepared by combining

| Ingredient | parts |
|---|---|
| Nonfat Milk | 96.4 |
| Amine Ester of Example 1 | 3.5 |
| Lecithin | 0.1 | mixing and homogenizing.

EXAMPLE 7

Cream Cheese. To make an imitation cream cheese, add

| Ingredient | parts |
|---|---|
| Water | 53 |
| Calcium Caseinate | 6.7 |
| Buttermilk Powder | 3.9 |
| Emulsifiers | 0.2 |
| Xanthan Gum | 0.2 | and mix three minutes. Melt

| Example 2 Amine Ester | 35.5 |
|---|---| and cook to 200° F. while mixing. Hold for one minute. Then cool to 150° F. and add

| Flavor, Acid and Color | 0.5 |
|---|---| and mix one minute. Fill, then cool and store.

EXAMPLE 8

Cheddar-Style Cheese. To make Cheddar-style cheese, homogenize

| Ingredient | parts |
|---|---|
| Nonfat Milk | 75.0 |
| Low Temperature Nonfat Dry Milk | 4.0 |
| Amine Ester of Example 3 | 20.0 |

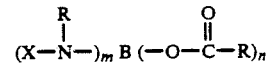

To this is added

| Salt | 0.7 |
|---|---|
| Lactic Acid Culture | 0.3 |

The mixture is fermented and pressed to a final composition of approximately 37.0% moisture, 63.0% total solids, and 32.0% fat mimetic.

EXAMPLE 9

Process Pimento Cheese Food. Processes pimento cheese food may be prepared by melting

| Ingredient | parts |
|---|---|
| Example 8 Cheddar Cheese | 43.0 |
| and Swiss cheese | 44.0 |

Into this is blended

| Dehydrated Pimento | 0.3 |
|---|---|
| and Water | 12.7 | and the mixture is cast into blocks.

EXAMPLE 10

Pudding. Pudding can be prepared from the following formulation:

| Ingredient | parts |
|---|---|
| Milk | 67 |
| Sugar | 11 |
| Starch | 5 |
| Water | 9 |
| Flavor | 3 |
| Example 2 Amine Ester | 5 |

The ingredients can be blended together and heated to form a pudding.

EXAMPLE 11

Mayonnaise. Mayonnaise may be prepared by adding

| Ingredient | parts |
|---|---|
| Water | 5.0 |
| to Sugar | 1.5 |

-continued

| Ingredient | parts |
|---|---|
| and Spices | 3.5 | and mixing three minutes. To this is added

| | |
|---|---|
| Salted Egg Yolks | 8.0 | followed by mixing two minutes, adding

| | |
|---|---|
| Amine Ester of Example 3 | 80.0 |
| then 120 Distilled Vinegar | 2.0 |

The mixture is blended 3 minutes and passed through a colloid mill set at 60 prior to filling in the usual process.

EXAMPLE 12

French Dressing. French Dressing may be prepared by adding

| Ingredient | parts |
|---|---|
| Water | 31.09 |
| Sugar | 15.00 |
| Salt | 2.50 |
| Spices | 2.40 |
| Xanthan Gum | 0.25 |
| Alginate | 0.14 |
| Polysorbate 60 | 0.12 | and mixing three minutes. Then

| | |
|---|---|
| 120 Distilled Vinegar | 12.00 |
| and Amine Ester of Example 1 | 36.50 | are added, mixed three minutes, and homogenized at 500 psi prior to filling in the usual process.

EXAMPLE 13

Dijon Mustard. A dijon-style mustard may be prepared by combining

| Ingredient | parts |
|---|---|
| Dry White Wine | 66.1 |
| with Water | 5.0 | and bringing to a boil. To this aqueous phase is added

| | |
|---|---|
| Ground, Defatted Yellow Mustard Seed | 12.4 |
| Amine Ester of Example 3 | 6.1 |
| Honey | 6.6 |
| Onion Powder | 2.0 |
| Salt | 1.3 |
| Garlic Powder | 0.3 |
| Mustard Oleo Resin | 0.2 |

The mixture is blended well, pasteurized and packaged.

EXAMPLE 14

Soda Crackers. Soda crackers may be prepared by pre-mixing ¼ of

| Ingredient | parts |
|---|---|
| Flour | 70.0 |
| Yeast | 0.2 | and sufficient water to make a dough. This is fermented for 24 hours. The remaining flour, enough water to make the total

| | |
|---|---|
| Water | 20.0 |
| Malt Syrup | 0.69 |
| Sodium Bicarbonate | 0.40 |
| Malt | 0.01 | are added and mixed well, the ferment added and mixed again. This is proofed for 8 hours, sheeted, and baked. Afterwards,

| | |
|---|---|
| Example 2 Amine Ester | 7.0 | is applied to the crackers, prior to packing, with

| | |
|---|---|
| Salt | 1.7 |

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims.

What is claimed is:

1. An edible composition comprising, in addition to other edible ingredients, a fat mimetic compound of the following formula:

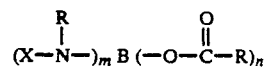

where
B is an aliphatic group having from 2 to 12 carbons,
each R is, independently, an aliphatic group having 1 to 30 carbons,
X=H or R, independently, m=1 to 2, and n=1 to 7.

2. A composition according to claim 1 wherein B has 2 to 6 carbons and R has 3 to 23 carbons.

3. A composition according to claim 2 wherein m=1, X is aliphatic, and n=2.

4. A composition according to claim 2 wherein m=2 and n=1 to 2.

5. A fat-containing food composition comprising, in addition to other edible ingredients, a fat mimetic of the following formula

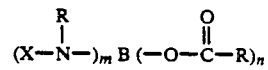

where

B is an aliphatic group having from 2 to 12 carbons, each R is, independently, an aliphatic group having 1 to 30 carbons, X=H or R, independently, m=1 to 2, and n=1 to 7 in full or partial replacement of said fat.

6. A composition according to claim 5 wherein B has 2 to 6 carbons, X is aliphatic, R has 3 to 23 carbons, m=1, and n=2.

7. A composition according to claim 5 wherein B has 2 to 6 carbons, R has 3 to 23 carbons, m=2 and n=1 or 2.

8. A composition according to claim 5 wherein said food composition is selected from the group consisting of dairy products, bakery products, and salad dressings.

9. A composition according to claim 5 wherein said fat mimetic delivers less than 9 kcal/gram upon being metabolized.

10. A composition according to claim 9 wherein said fat mimetic delivers less than 5 kcal/gram upon being metabolized.

11. A composition according to claims 1 or 5 wherein R has 3 to 23 carbons.

12. A composition according to claim 11 wherein 95% of the R groups include groups derived from acids having 14 to 18 carbons.

13. An edible composition comprising, in addition to other edible ingredients, a fat mimetic compound of the following formula:

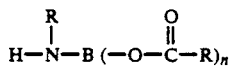

where
B is an aliphatic group having 2 to 6 carbons, each R is, independently, an aliphatic group having 3 to 23 carbons,
n=1 to 5.

14. A composition according to claims 1, 5 or 13 wherein R is derived from acids selected from the group consisting of propionic, butyric, caproic, caprylic, pelargonic, capric, undecanoic, lauric, myristic, palmitic, stearic, arachidic, behenic, erucic, brassidic, lignoceric, cerotic, montanic, melissic, palmitoleic, oleic, vaccenic, linoleic, linolenic, eleostearic, arachidonic, nervonic, eicosapentaenoic, docosatetraenoic, docosapentaenoic, and docosahexaenoic acid, and mixtures thereof.

15. A composition according to claims 1, 5 or 13 wherein R is derived from mixtures of acids obtained from the hydrolysis of non-hydrogenated, partially hydrogenated or fully hydrogenated oils selected from the group consisting of soybean, safflower, sunflower, sesame, peanut, corn, olive, rice bran, canola, babassu nut, coconut, palm, palm kernel, lupin, nasturtium seed, mustard seed, cottonseed, low erucic rapeseed, dairy butter and marine oil, and fractions thereof.

16. An edible composition comprising, in addition to other edible ingredients, an amine ester compound having a $C_2$ to $C_6$ aliphatic backbone to which is attached one $C_1$ to $C_{30}$ aliphatic group in amine linkage and one or two $C_1$ to $C_{30}$ aliphatic groups in ester linkage.

17. A composition according to claim 16 having two $C_3$ to $C_{23}$ aliphatic groups in ester linkage.

18. A method of reducing the calories in a food composition having an edible fat component, which method comprises formulating said composition with a fat mimetic of the formula:

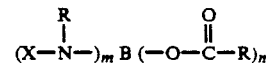

where
B is an aliphatic group having from 2 to 12 carbons, each R is, independently, an aliphatic group having 1 to 30 carbons,
X=H or R, independently,
m=1 to 2, and
n=1 to 7 in full or partial replacement of said fat component.

19. A method according to claim 18 wherein B has 2 to 6 carbons, m=1, X is aliphatic, n=2, and R has 3 to 23 carbons.

20. In a food composition containing a fat ingredient, an improvement wherein at least a portion of said fat ingredient is replaced by a fat mimetic of the formula:

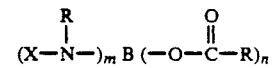

where
B is an aliphatic group having from 2 to 12 carbons, each R is, independently, an aliphatic group having 3 to 23 carbons,
X=H or R, independently,
m=1 to 2, and
n=1 to 7.

21. An improvement according to claim 20 wherein said fat mimetic delivers less than 5 kcal/gram.

22. An improvement according to claim 20 wherein said fat mimetic has an array of R groups selected to include 95% derived from acids having 14 to 18 carbon atoms.

23. An improvement according to claim 20 wherein B has 2 to 6 carbons, m=1, n=2, and X=H.

* * * * *